United States Patent [19]
Shiota

[11] Patent Number: 5,706,828
[45] Date of Patent: Jan. 13, 1998

[54] SUDORIFIC MASK

[75] Inventor: Natsumi Shiota, Choofu, Japan

[73] Assignee: Mike Corporation, Tokyo, Japan

[21] Appl. No.: 681,990

[22] Filed: Jul. 30, 1996

[51] Int. Cl.$^6$ ................................. A61F 11/00
[52] U.S. Cl. ............................. 128/857; 2/9
[58] Field of Search ....................... 128/846, 857, 128/858; 2/9, 410, 173, 174, 202

[56]  References Cited

U.S. PATENT DOCUMENTS

| 1,333,438 | 3/1920 | Moore | 2/9 |
| 1,584,012 | 5/1926 | Cocroft | 2/9 |
| 4,095,290 | 6/1978 | O'Brien | 2/9 |
| 4,117,837 | 10/1978 | MassóRemiro | 600/38 |

Primary Examiner—Michael A. Brown
Attorney, Agent, or Firm—Oblon, Spivak, McClelland, Maier & Neustadt, P. C.

[57]  ABSTRACT

A sudorific mask is composed of a body which has openings corresponding to the eyes, a profile cut corresponding to the nose, an opening corresponding to the mouth, and cuts. The sudorific mask can be readily attached to the face to generate perspiration on the face. The openings and the profile cut allow a user to see and talk while the user is wearing the sudorific mask. The sudorific mask increases perspiration on the facial skin in a comfortable manner.

3 Claims, 5 Drawing Sheets

SUDORIFIC MASK

BACKGROUND OF THE INVENTION

1. Field of the Invention

The present invention relates to a sudorific mask which is put on one's face to increase perspiration.

2. Description of the Related Art

Conventional facial treatment includes the following methods: a face pack is applied to the face and then the dried face pack is peeled off or washed away; alternatively, dirt is sucked from the facial skin using a tool.

However, since these methods are intended to remove dirt from the facial skin, it is to be expected that these methods fail to induce a sudorific action, an associated promotion of the facial skin metabolism, and an associated effect of making the face skin taut.

SUMMARY OF THE INVENTION

The present invention has been accomplished in view of the above-described problems. An object of the present invention is to provide a sudorific mask for increasing perspiration on the facial skin.

In order to achieve the above object, the present invention provides a sudorific mask which has cut portions at least at positions corresponding to the eyes, the nose, and the mouth and which is put on the face to increase perspiration on the face.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DESCRIPTION OF THE PREFERRED EMBODIMENTS

Figure 1:
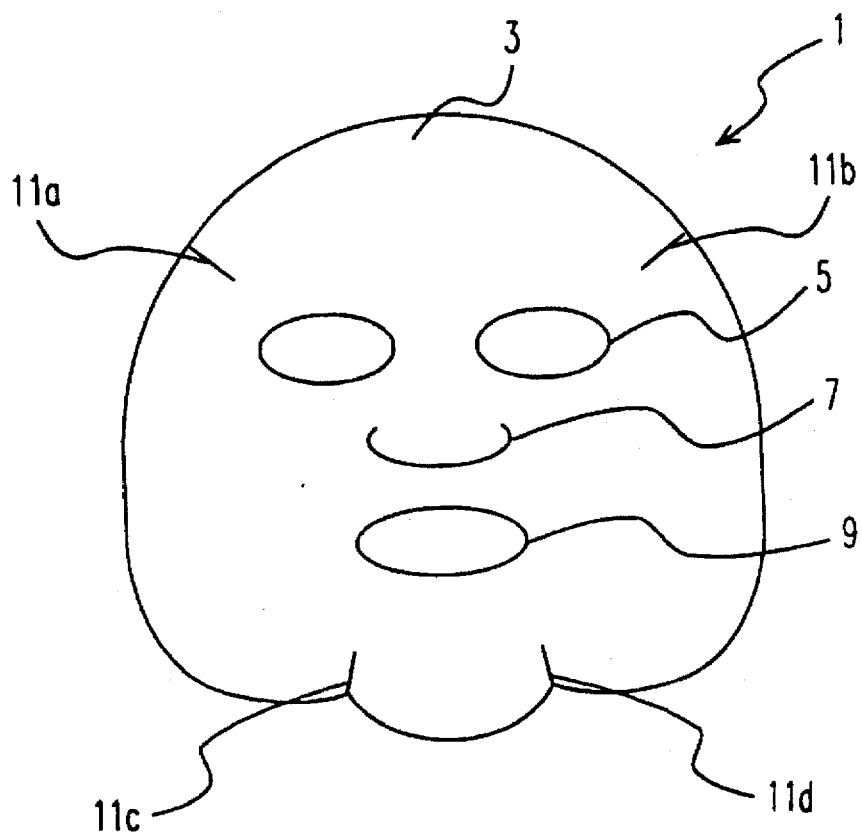
FIG. 1 is a front view showing a sudorific mask according to a first embodiment of the present invention.
Figure 2:
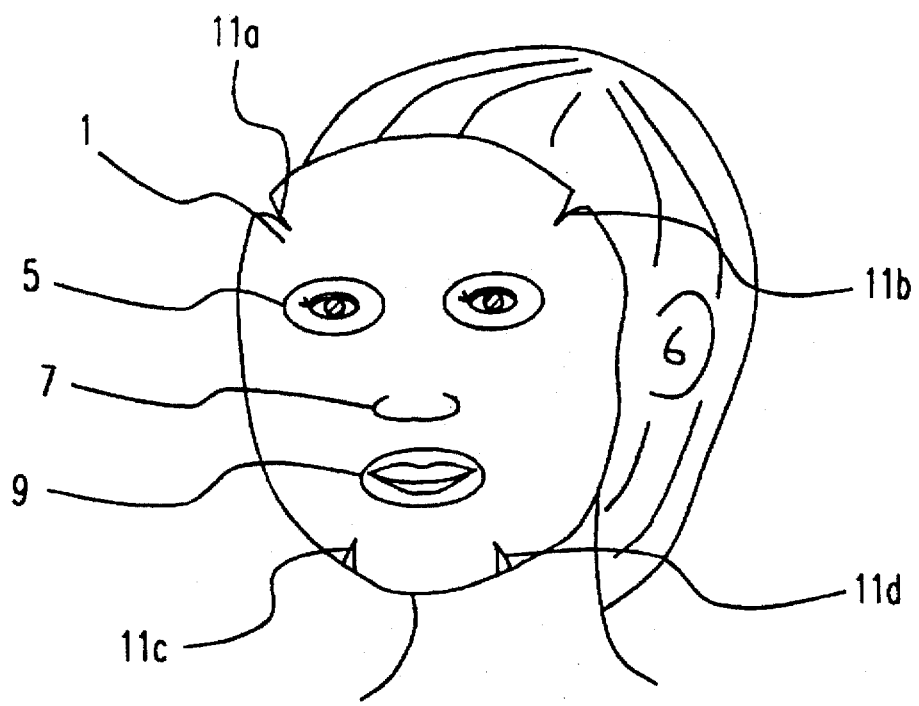
FIG. 2 is a perspective view showing the sudorific mask according to the first embodiment which is put on a face.

A first embodiment of the present invention will now be described in detail with reference to the drawings. FIG. 1 shows a sudorific mask 1 according to the first embodiment. FIG. 2 shows the sudorific mask 1 which is put on the face. As shown in FIG. 1, the sudorific mask 1 comprises a body 3 on which are formed opening 5, a profile cut 7, an opening 9, and cuts 11a, 11b, 11c, and 11d.

The body 3 is made of vinyl such as polyethylene and is approximately 0.02 mm thick. When the sudorific mask 1 is put on the face, the body 3 closely contacts the face while the openings 5 allow the eyes to not be blocked, the profile cut 7 allows the nose to not be blocked, and the opening 9 allows the mouth to not be blocked. The cuts 11a and 11b serve as improving the degree of contact of the body 3 with a forehead, and the cuts 11c and 11d serve to improve the degree of contact of the body 3 with the chin. That is, the cuts 11 allow the body 3 to closely contact the face.

The usage of the sudorific mask 1 will be next described. FIG. 2 shows the sudorific mask 1 which is put on the face. A user puts the sudorific mask 1 on his/her face while pressing it with his/her hands. This brings the sudorific mask 1 in close contact with the face due to perspiration. Application of cream or the like to the face will establish closer contact between the sudorific mask 1 and the face. The sudorific mask 1 can be readily removed from the face with the user's hand.

As shown in FIG. 2, while the sudorific mask 1 is being put on the face, the openings 5, the profile cut 7, and the opening 9 allow the user to see, breathe, and talk, respectively. Perspiration, which is increased by wearing the sudorific mask 1, can be expected to promote the facial skin metabolism as well as to make the facial skin taut.

A user can wear the sudorific mask 1 not only in a room but while taking a bath. For example, before taking a bath, the user applies cream or the like to his/her face and puts the sudorific mask 1 on the face. While the sudorific mask 1 is being put on the face, the user can see and talk. Also, the user can get in a bathtub and wash his/her body while the sudorific mask 1 is being put on the face. After taking a bath, the user removes the sudorific mask 1 from the face and washes the face.

Figure 3:
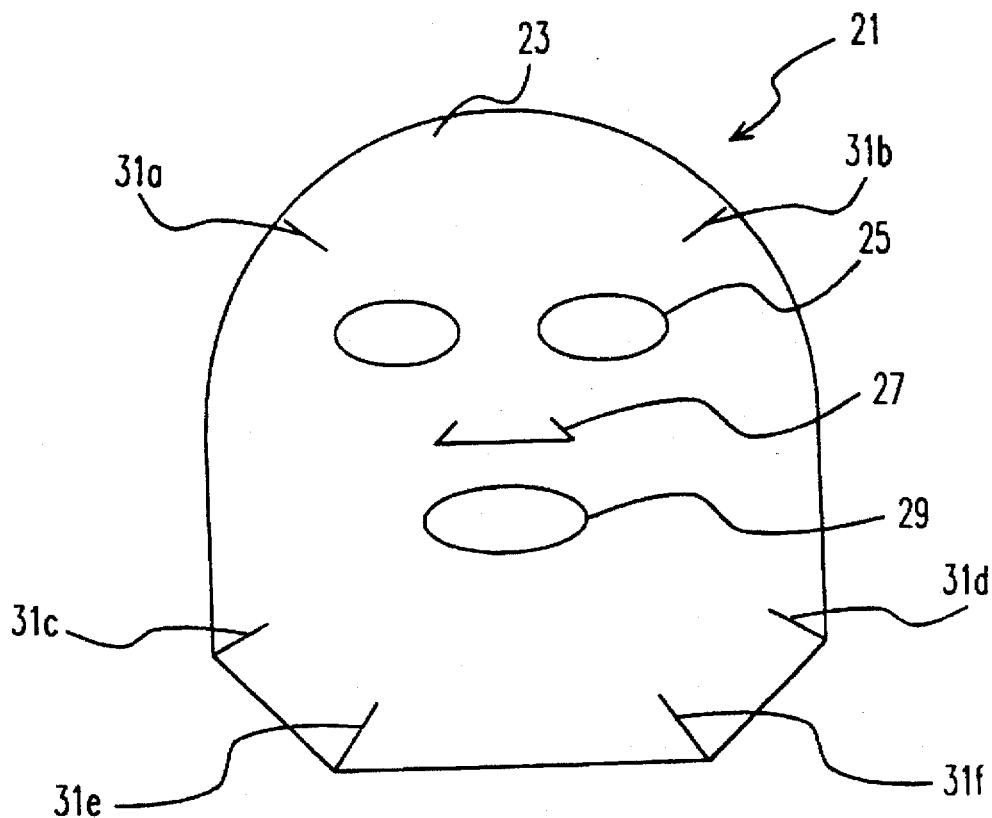
FIG. 3 is a front view showing a sudorific mask according to a second embodiment of the present invention.

Sudorific masks according to other embodiments of the present invention will next be described with reference to FIGS. 3, 4, 5, 6, 7, 8, and 9. FIG. 3 shows a sudorific mask 21 according to a second embodiment of the present invention. As shown in FIG. 3, the sudorific mask 21 comprises a body 23 on which are formed openings 25, a profile cut 27, an opening 29, and cuts 31a, 31b, 31c, 31d, 31e, and 31f. The cuts 31c and 31d corresponding to the cheeks allow the body 23 to closely fit the cheeks.

Figure 4:
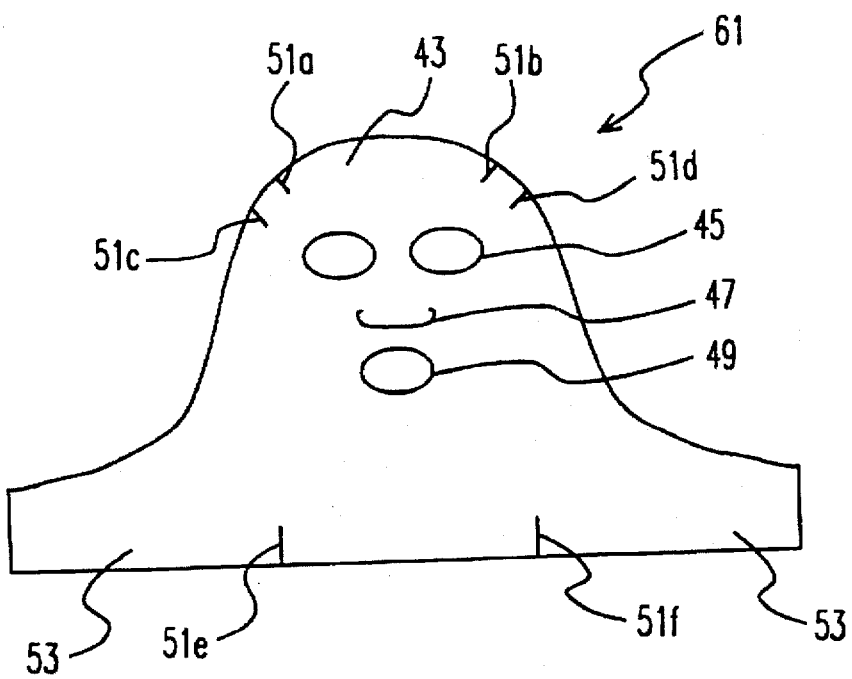
FIG. 4 is a front view showing a sudorific mask according to a third embodiment of the present invention.

FIG. 4 shows a sudorific mask 41 according to a third embodiment of the present invention. As shown in FIG. 4, the sudorific mask 41 comprises a body 43 on which are formed openings 45, a profile cut 47, an opening 49, and cuts 51a, 51b, 5c, 51d, 51e, and 51f. Further, projecting portions 53 are formed at the lower portion of the body 43. The cuts 51a, 51b, 51c, and 51d, which correspond to the forehead, allow the body 43 to readily fit the forehead. The projecting portions 53 are wound around a user's neck so as to increase perspiration on the neck skin.

Figure 5:
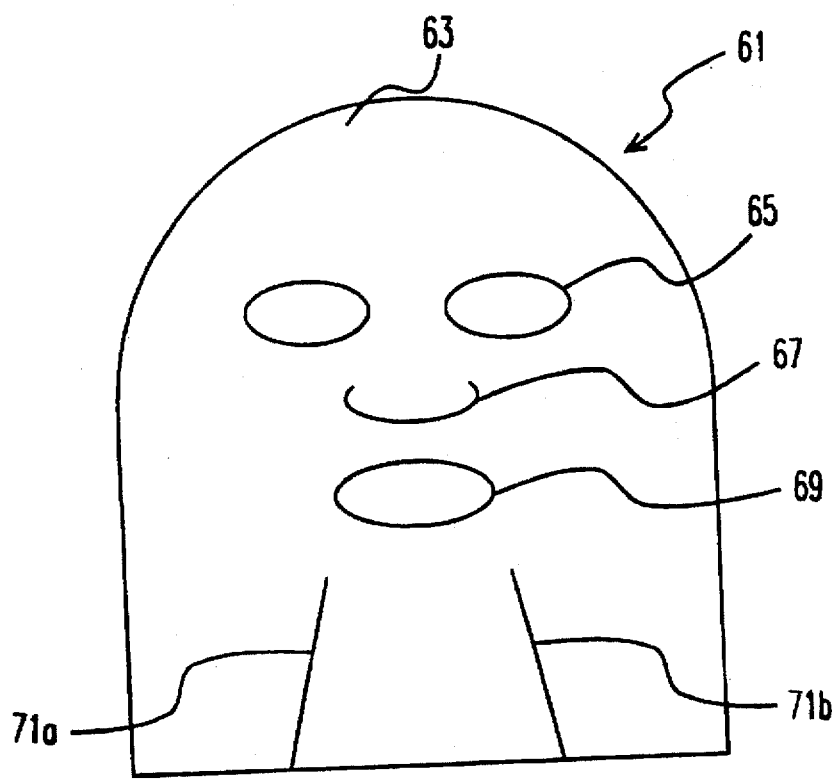
FIG. 5 is a front view showing a sudorific mask according to a fourth embodiment of the present invention.

FIG. 5 shows a sudorific mask 61 according to a fourth embodiment of the present invention. As shown in FIG. 5, the sudorific mask 61 comprises a body 63 on which are formed openings 65, a profile cut 67, an opening 69, and cuts 71a and 71b. The body 63 is vertically elongated, and its lower portion is shaped so as to be squarish. Thus, the body 63 can cover a relatively wide area located at the bottom of the chin, thereby increasing perspiration on the corresponding skin.

Figure 6:
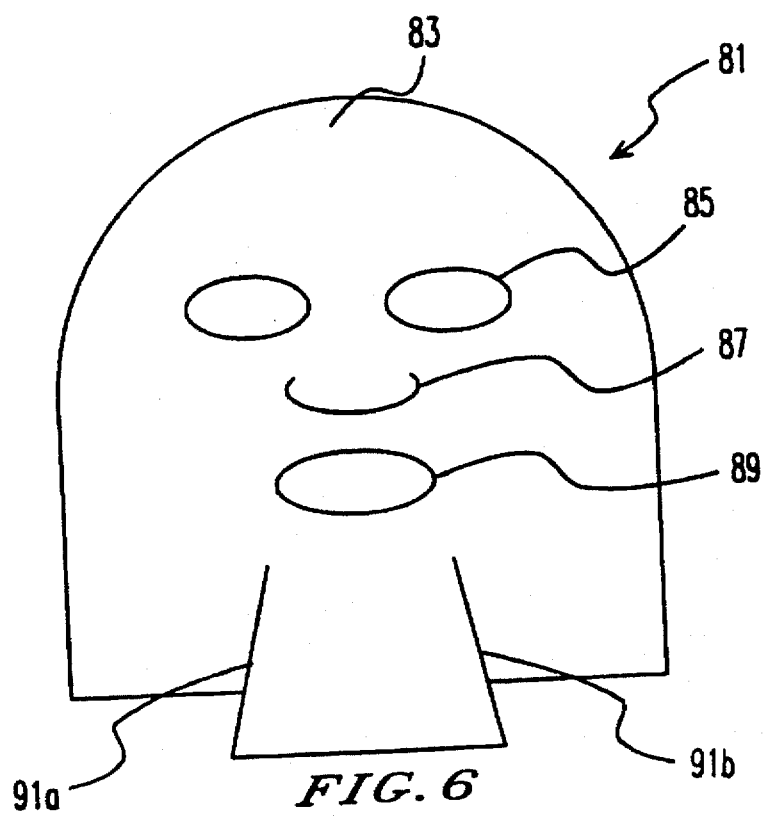
FIG. 6 is a front view showing a sudorific mask according to a fifth embodiment of the present invention.

FIG. 6 shows a sudorific mask 81 according to a fifth embodiment of the present invention. As shown in FIG. 6, the sudorific mask 81 comprises a body 83 on which are formed openings 85, a profile cut 87, an opening 89, and cuts 91a and 91b. The sudorific mask 81 can increase perspiration on the bottom skin of the chin as well as on the facial skin.

Figure 7:
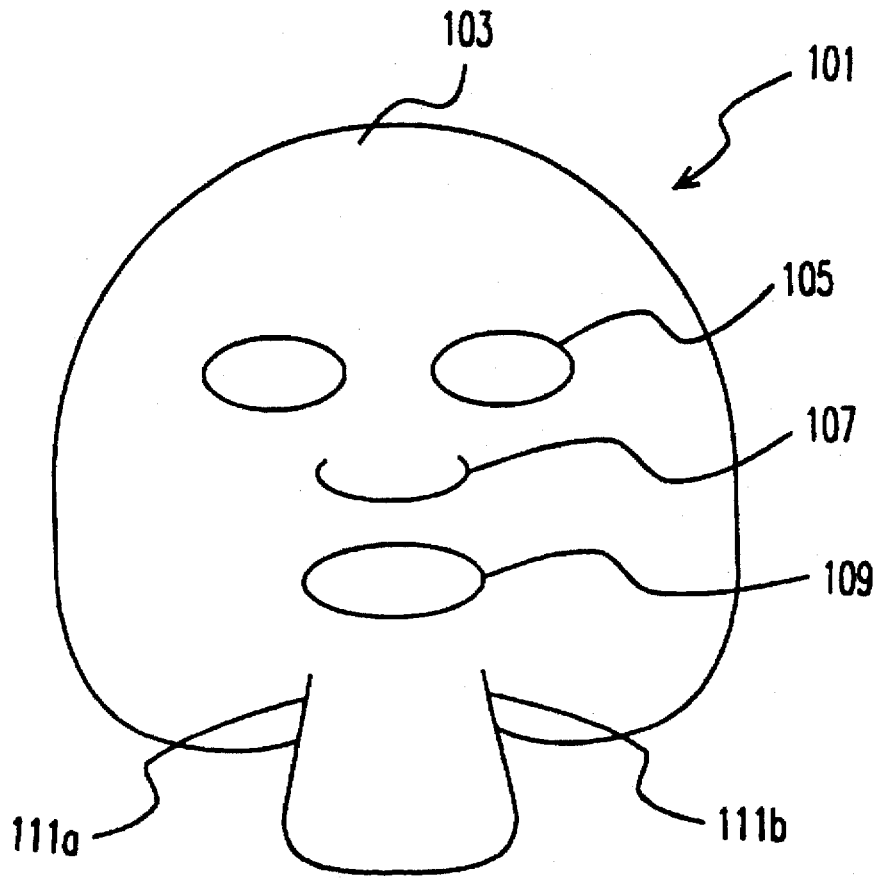
FIG. 7 is a front view showing a sudorific mask according to a sixth embodiment of the present invention.

FIG. 7 shows a sudorific mask 101 according to a sixth embodiment of the present invention. As shown in FIG. 7, the sudorific mask 101 comprises a body 103 on which are formed openings 105, a profile cut 107, an opening 109, and cuts 111a and 111b.

Figure 8:
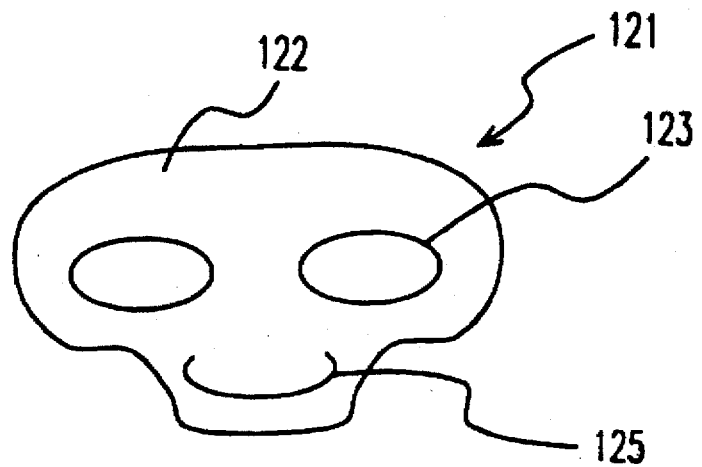
FIG. 8 is a front view showing a sudorific mask according to a seventh embodiment of the present invention.

FIG. 8 shows a sudorific mask 121 according to a seventh embodiment of the present invention. As shown in FIG. 8, the sudorific mask 121 comprises a body 122 on which are formed openings 123 and a profile cut 125. The openings 123 allow the eyes to not be blocked, and the profile cut 125 allows the nose to not be blocked. The body 122 is put on the upper portion of the face so as to increase perspiration on the corresponding facial skin.

Figure 9:
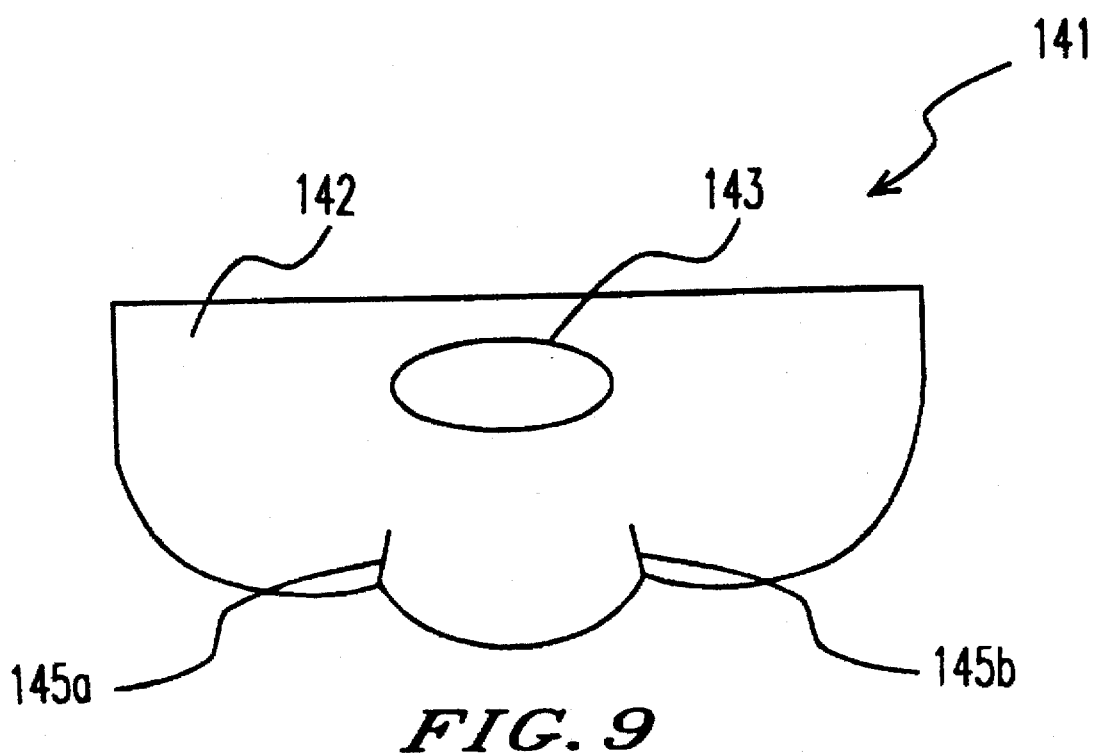
FIG. 9 is a front view showing a sudorific mask according to an eighth embodiment of the present invention.

FIG. 9 shows a sudorific mask 141 according to an eighth embodiment of the present invention. As shown in FIG. 9, the sudorific mask 141 comprises a body 142 on which are formed an opening 143 and cuts 145a and 145b. The opening 143 allows the mouth to not be blocked. The body 142 is put on the lower portion of the face so as to increase perspiration on the corresponding facial skin. The sudorific masks 121 and 141 may be used separately or together.

As described above, a sudorific mask according to each embodiment can be readily attached to the face with moisture such as perspiration and can be easily removed from the face. Further, while the sudorific mask is being put on the face, the eyes, the nose, and the mouth are not blocked, so that a user can see and talk.

What is claimed is:

1. A sudorific mask made of vinyl, the sudorific mask having a thickness of approximately 0.02 mm, and comprising;

a body which has cut portion at least at positions corresponding to the eyes, nose, and mouth of a wearer, said body being put on the face and increasing perspiration on a face portion of the wearer, said body covering mainly the face portion of the wearer.

2. A sudorific mask made of vinyl, the sudorific mask having a thickness of approximately 0.02 mm, and comprising a body which has cut portion at least at positions corresponding to the eyes and nose of a wearer, said body being put on the face of the wearer and increasing perspiration on a face portion of the wearer, and said body covering an upper portion of the face portion of the wearer.

3. A sudorific mask made of vinyl, the sudorific mask having a thickness of approximately 0.02 mm and comprising: a body which has cut portion at least at positions corresponding to a mouth of the wearer, said body being put on a face portion of the wearer and increasing perspiration on the face portion, and said body covering a lower portion of the face portion of the wearer.

\* \* \* \* \*